US010470735B2

(12) United States Patent
Mentrup et al.

(10) Patent No.: US 10,470,735 B2
(45) Date of Patent: Nov. 12, 2019

(54) DEVICE AND METHOD FOR SIGNAL COMPENSATION IN MEDICAL X-RAY IMAGES

(71) Applicant: KONINKLIJKE PHILIPS N.V., Eindhoven (NL)

(72) Inventors: Detlef Mentrup, Hamburg (DE); Hanns-Ingo Maack, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 3 days.

(21) Appl. No.: 15/531,634

(22) PCT Filed: Nov. 23, 2015

(86) PCT No.: PCT/EP2015/077322
§ 371 (c)(1),
(2) Date: May 30, 2017

(87) PCT Pub. No.: WO2016/087242
PCT Pub. Date: Jun. 9, 2016

(65) Prior Publication Data
US 2017/0325774 A1 Nov. 16, 2017

(30) Foreign Application Priority Data

Dec. 3, 2014 (EP) .................................. 14196077

(51) Int. Cl.
*A61B 6/00* (2006.01)
*H04N 5/32* (2006.01)
*H04N 5/359* (2011.01)

(52) U.S. Cl.
CPC ............. *A61B 6/5258* (2013.01); *H04N 5/32* (2013.01); *H04N 5/359* (2013.01)

(58) Field of Classification Search
None
See application file for complete search history.

(56) References Cited

U.S. PATENT DOCUMENTS 5,920,070 A * 7/1999 Petrick .................. H04N 5/325
250/370.09
6,895,077 B2 5/2005 Karellas
(Continued)

OTHER PUBLICATIONS

Siewerdsen, J.H. et al "Empirical and Theoretical Investigation of the Noise Performance of Indirect Detection, Active Matrix Flat-Panel Imagers (AMFPIs) for Diagnostic Radiology", Medical Phys. vol. 24, No. 1, Jan. 1997.
(Continued)

*Primary Examiner* — Kevin Ky
(74) *Attorney, Agent, or Firm* — Larry Liberchuk

(57) ABSTRACT

The present invention relates to a device for signal compensation in medical X-ray images. The device (100) comprises a generation module (10) configured to generate an X-ray ghosting image based on an X-ray detector read-out subsequent to a last X-ray exposure of a plurality of X-ray exposures; a scaling module (20) configured to scale the X-ray ghosting image into a scaled X-ray ghosting image; and a subtraction module (30) configured to subtract the scaled X-ray ghosting image from any subsequent X-ray image recorded during a respective subsequent X-ray exposure of the plurality of X-ray exposures.

13 Claims, 7 Drawing Sheets

(56) References Cited

U.S. PATENT DOCUMENTS

| | | | |
|---|---|---|---|
| 7,277,568 B2 | 10/2007 | Spahn | |
| 9,579,790 B2* | 2/2017 | Laurent | |
| 2002/0064254 A1* | 5/2002 | Aoki | A61B 6/00 |
| | | | 378/98.7 |
| 2005/0151086 A1 | 7/2005 | Spahn | |
| 2007/0040099 A1 | 2/2007 | Yokoyama | |
| 2007/0122025 A1* | 5/2007 | Christian | G06K 9/4609 |
| | | | 382/141 |
| 2007/0291900 A1* | 12/2007 | Hahm | G06T 5/50 |
| | | | 378/98.8 |
| 2009/0060138 A1* | 3/2009 | Van De Haar | A61B 6/583 |
| | | | 378/116 |
| 2010/0006767 A1 | 1/2010 | Enomoto | |
| 2012/0138808 A1 | 6/2012 | Jung | |
| 2016/0058403 A1* | 3/2016 | Kim | A61B 6/469 |
| | | | 378/62 |
| 2016/0075034 A1* | 3/2016 | Laurent | H04L 12/282 |
| | | | 700/264 |

OTHER PUBLICATIONS

Marshall, N.W. et al "Quality Control Measurements for Digital X-Ray Detectors", Physics in Medicine and Biology, vol. 56, 2011, pp. 979-999.

Marshall, N.W. et al, "Measurement and Correction of the Effects of Lag on Contrast-Detail Test Results in Fluoroscopy", Physics in Medicine and Biology, vol. 47, 2002, pp. 947-960.

Overdick, M. et al, "Temporal Artifacts in Flat Dynamic X-Ray Detectors", Proc. SPIE vol. 4320, pp. 47-58, 2001.

* cited by examiner

DEVICE AND METHOD FOR SIGNAL COMPENSATION IN MEDICAL X-RAY IMAGES

CROSS-REFERENCE TO PRIOR APPLICATIONS

This application is the U.S. National Phase application under 35 U.S.C. § 371 of International Application No. PCT/EP2015/077322, filed on Nov. 23, 2015, which claims the benefit of European Patent Application No. 14196077.3, filed on Dec. 3, 2014. These applications are hereby incorporated by reference herein.

FIELD OF THE INVENTION

The present invention relates to compensation in medical X-ray images of signals caused by flat panel X-ray detectors. In particular, the present invention relates to a device and a method for such signal compensation.

BACKGROUND OF THE INVENTION

US 2012/0138808 A1 describes an X-ray detector and a method for controlling the X-ray detector, which method compensates for an image lag by using an X-ray image and a dark image wherein the dark image is separately provided. A standby time for the X-ray scanning may be reduced by increasing the accuracy of the image lag compensation.

U.S. Pat. No. 7,277,568 B2 describes a method for suppressing ghost image artefacts in X-ray images. In chronological order, a plurality of X-ray images of one or more objects is generated with the interposition of at least one solid-state detector for generating a visible image in response to incident X-ray radiation. From each generated X-ray image, a previously ascertained correction image is electronically subtracted.

U.S. Pat. No. 6,895,077 B2 describes a system for X-ray fluoroscopic imaging of bodily tissue in which a scintillation screen and a charge coupled device, CCD, is used to image selected tissue. An X-ray source generates X-rays which pass through a region of a subject's body, forming an X-ray image which reaches the scintillation screen.

US 2010/0006767 A1 discloses a radiographic imaging system configured for suppressing ghost image artefacts during image stitching procedures employing a plurality of dark images.

US 2007/0291900 A1 discloses a method for suppressing ghost image artefacts employing a plurality of dark images.

When performing radiographic imaging with a flat panel detector, high X-ray doses and a short time in between the X-ray exposures may result in the visibility of memory artefacts ("lag" or "ghosting"), since the known offset correction methods perform poorly. Visibility of residual signals, i.e. ghosting after high-dose X-ray exposure, is a well-known problem in flat panel X-ray detectors. Conventional methods suggest to compensate for ghosting by subtracting from the image of the patient an offset image obtained by an X-ray detector read-out after X-ray exposure.

SUMMARY OF THE INVENTION

There may be a need to improve compensation in medical X-ray or radiographic images of signals caused by flat panel X-ray detectors.

These needs are met by the subject-matter of the independent claims. Further exemplary embodiments are evident from the dependent claims and the following description.

An aspect of the present invention relates to a device for signal compensation in medical X-ray image. This device comprises a generation module configured to generate an X-ray ghosting image based on an X-ray detector read-out subsequent to a last X-ray exposure of a plurality of X-ray exposures; a scaling module configured to scale the X-ray ghosting image into a scaled X-ray ghosting image; and a subtraction module configured to subtract the scaled X-ray ghosting image from any subsequent X-ray image recorded during a respective subsequent X-ray exposure of the plurality of X-ray exposures.

The term "subsequent X-ray exposure" as used by the present invention may refer to any X-ray exposure, of a plurality of X-ray exposures performed after the first X-ray exposure, up to and including the last X-ray exposure of said plurality of X-ray exposures.

The term "subsequent X-ray image" as used by the present invention may refer to any X-ray image, of a plurality of X-ray images recorded after the first X-ray image, up to and including (but not beyond) the last X-ray image of said plurality of X-ray images.

The term "X-ray ghosting image" as used by the present invention may refer to any replica of a first (or more generally a prior) X-ray image and that is super-imposed on top of a second (or more generally a subsequent) X-ray image due to any image sensor memory effect. The electrical signature of an X-ray image with high brightness levels that falls onto a semiconductor image sensor, for instance, may remain embedded in subsequently read-out electrical signatures of subsequently acquired images. The electrical signature of a previously sensed image remaining in the image sensor may be referred to as "ghost artefact" or "ghost image" or as a memory effect.

The term "scaling the X-ray ghosting image" as used by the present invention may refer to a scaling of the X-ray ghosting image, either in the form of a signal or image data, with one or more factors. Such factors may depend on time intervals between the prior and post read-out of the X-ray detector, or may depend on time intervals established by the points in time of consecutive X-ray exposures. Alternatively, the factor may be determined by using the criterion of minimization of image variance, or any combination of both.

The present invention advantageously proposes to make the compensation dependent on a time-dependent decay of the residual signal. The present invention advantageously proposes to generate an X-ray ghosting image rather than an offset image, to scale the ghosting image, and to subtract the scaled X-ray ghosting image from the image of the patient. The present invention consequently advantageously circumvents a mismatch between (i) the offset or lag value at the time of the X-ray detector read-out of the exposed image and (ii) the offset or lag value at the time of the X-ray detector read-out of a dark image or offset image.

Further advantageous embodiments of the present invention are represented by the dependent claims. In an exemplary embodiment of the present invention, the generation module is furthermore configured to generate the X-ray ghosting image based on an X-ray detector read-out prior to a first X-ray exposure of the plurality of X-ray exposures. This embodiment advantageously allows that such X-ray ghosting image is obtained by subtracting, from the detector read-out made after X-ray exposure, a detector read-out made prior to X-ray exposure. This subtraction will exactly yield the residual signal at the point in time at which the read-out after the exposure is performed.

In a further exemplary embodiment of the present invention, the subtraction module is furthermore configured to subtract, from a first X-ray image recorded during the first X-ray exposure and/or any subsequent X-ray image, the X-ray detector read-out prior to said first X-ray exposure. This embodiment advantageously allows that such first and any such subsequent X-ray image is corrected for offset similar to the X-ray ghosting image.

A further exemplary embodiment of the present invention suggests a procedure, applied to the X-ray ghosting image, to remove the artefacts optimally and in particular with regard to the time period between the recordings of consecutive X-ray images. The artefact is measured and optimally scaled, such that the resulting image contains a minimum residual of artefacts.

In a further exemplary embodiment of the present invention, the scaling module is configured to employ a scaling that is based on a time period between (i) the X-ray detector read-out subsequent to the last X-ray exposure and the first X-ray exposure and/or (ii) the first X-ray exposure and any subsequent X-ray exposure. For instance, the actual time period—may be a time period of up to 5 seconds, a time period of up to 30 seconds, or a time period of up to 120 seconds. This advantageously allows an optimal adaption of the artefact correction depending on an individual timing of the image acquisition.

In a further exemplary embodiment of the present invention, the scaling module is configured to employ a scaling that is based on a time period between (i) the X-ray detector read-out subsequent to the last X-ray exposure and the first X-ray exposure and/or (ii) the first X-ray exposure and the second X-ray exposure.

In a further exemplary embodiment of the present invention, the scaling module is configured to scale the X-ray ghosting image employing a scaling that is based on minimization of a calculated image variance of at least one (i.e. one or more) subsequent X-ray image(s). Herein, the term "image variance" may refer to the variance within adjacent pixels, for instance within a square array of pixels surrounding a specific position or a specific pixel. This advantageously allows a safe and reliable method for reducing artefacts and signal lags on the X-ray image of the patient.

In a further exemplary embodiment of the present invention the scaling module is configured to scale the X-ray ghosting image employing a scaling that is different for each subsequent X-ray image. This embodiment advantageously enables a scaling tailored towards each subsequent X-ray image.

A further exemplary embodiment of the present invention allows that such X-ray ghosting image is obtained by detecting in the prior image the areas of high dose which will cause a memory effect in a subsequent image. This detection may be carried out, e.g., by thresholding the pixel values in the prior image. The present invention is advantageously employed during recording or acquiring of radiographic images with a flat panel X-ray detector, wherein high doses are used and a short time, for instance less than 5 seconds, less than 30 seconds or less than 120 seconds, is given between the X-ray exposures of two images wherein the X-ray exposures may result in the visibility of memory artefacts, also called lag, since the known offset correction methods do not allow to subtract these artefacts.

Due to the fast decay of the lag signal with time, there is a mismatch between the offset value at the time of the read-out of the exposed image and at the time of the X-ray detector read-out subsequent to the last X-ray exposure. The decay of the lag signal may be in time scales of 5 seconds or 30 seconds or 120 seconds or in comparable order of magnitude. The decay may be described by an exponential decay function, by a hyperbolic decay function or by a polynomial function. The lag signal may be inversely proportional or quasi-inversely proportional with time.

According to an exemplary embodiment of the present invention, the subtraction module is configured to subtract the scaled X-ray ghosting image from any subsequent X-ray image acquired subsequently with a movable flat-panel X-ray detector.

According to an exemplary embodiment of the present invention, the subtraction module is configured to subtract the scaled X-ray ghosting image from any subsequent X-ray image by using at least one scaling factor.

According to a further, second aspect of the present invention, a medical imaging system is provided comprising a flat panel X-ray detector and a device according to the first aspect or according to any implementation form of the first aspect of the present invention.

According to an exemplary embodiment of the present invention, the flat panel X-ray detector is a movable flat-panel X-ray detector.

According to an exemplary embodiment of the present invention, the medical imaging system is configured to perform image stitching by combining multiple images with overlapping fields of view to produce a joined image.

According to a further, third aspect of the present invention, a method for signal compensation of medical X-ray images is provided. This method comprises: a step of generating, by means of a generation module, an X-ray ghosting image based on an X-ray detector read-out subsequent to a last X-ray exposure of a plurality of X-ray exposures; a step of scaling, by means of a scaling module, the X-ray ghosting image into a scaled X-ray ghosting image; and a step of subtracting, by means of a subtraction module, the scaled X-ray ghosting image from any subsequent X-ray image recorded during a respective subsequent X-ray exposure of the plurality of X-ray exposures.

Further advantageous embodiments of the present invention are represented by the dependent claims.

In a further exemplary embodiment of the present invention, the step of generating is furthermore configured for generating the X-ray ghosting image based on an X-ray detector read-out prior to a first X-ray exposure of the plurality of X-ray exposures.

A further exemplary embodiment of the present invention furthermore comprises a step for subtracting, by means of the subtraction module, the X-ray detector read-out prior to the first X-ray exposure from a first X-ray image recorded during said first X-ray exposure and/or from any subsequent X-ray image.

In a further exemplary embodiment of the present invention, the step of scaling is performed employing a scaling that is based on minimization of a calculated image variance of at least one (i.e. one or more) subsequent X-ray image(s).

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, abbreviated ASIC.

The present invention can be implemented in digital electronic circuitry, or in computer hardware, firmware, software, or in combinations thereof, e.g. in available hardware of medical devices or in new hardware dedicated for processing the methods described herein.

A more complete appreciation of the present invention and the advantages thereof will be more clearly understood by reference to the following schematic drawings, which are not to scale, wherein.

DETAILED DESCRIPTION OF EMBODIMENTS

Figure 1:
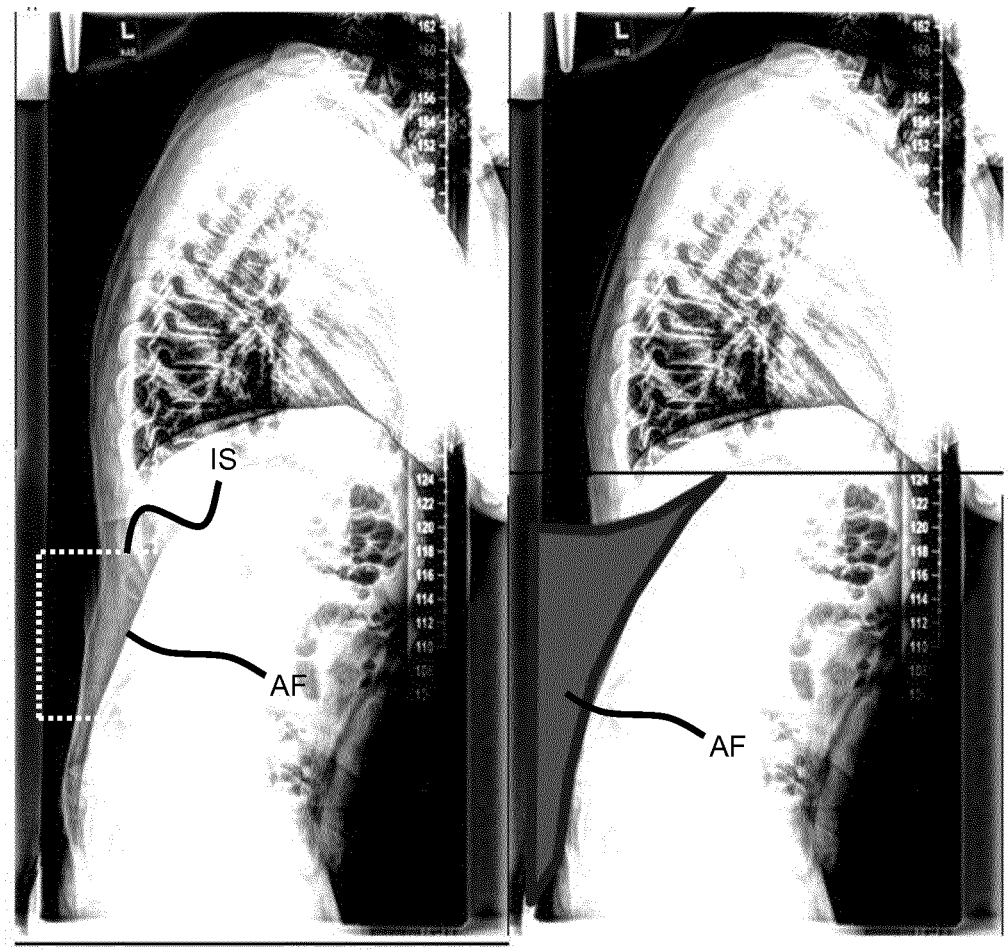
FIG. 1 shows a schematic image of a lag visibility in the clinical stitched lateral spine X-ray exposure for explaining the present invention.

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

FIG. 1 shows two schematic images of a lag visibility in the clinical stitched lateral spine X-ray exposure for explaining the present invention. FIG. 1 shows clinical examples. In the upper part of the right image of FIG. 1, there is a body contour that leads to an artefact as presented below, which artefact comes into being because image stitching is performed. The area exposed to high X-ray dose direct radiation in the upper part due to the recording of the image as shown on the left image of FIG. 1, leads to an artefact AF in the image section IS in the lower part of the X-ray image which lower part is subsequently recorded. That is: the contour of the shoulder appears in the abdominal area of the image as an X-ray ghosting image or artefact AF as also shown with more emphasis on the right image of FIG. 1.

Figure 2:
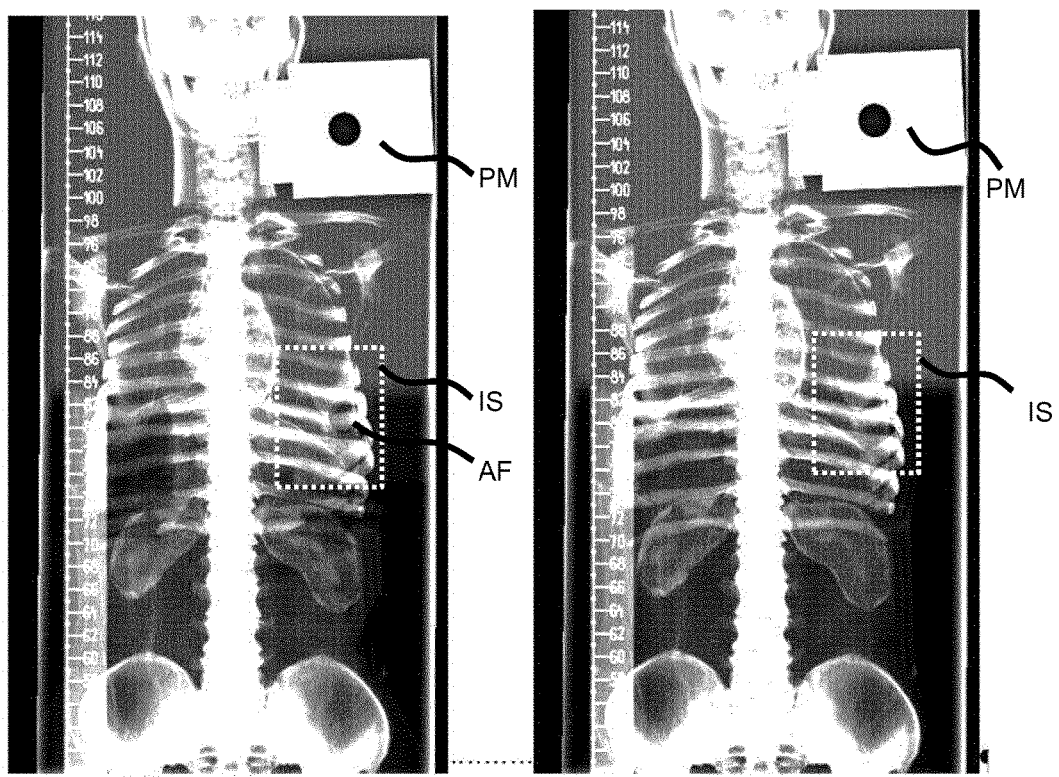
FIG. 2 shows stitched X-ray images, the first of which is recorded with a status quo method and the second of which is recorded with the method according to present invention.

FIG. 2 shows a stitched X-ray image recorded with different methods for explaining the present invention. FIG. 2 shows an effect of this invention on a stitched X-ray image. The left image in FIG. 2 shows the status quo for medical imaging systems. A sharp dose transition in the first image is present which result in ghosting artefacts AF within an image section IS of the second image. The artefact AF is due to a sharp contrast variation caused by a position marker PM. The right image of FIG. 2 depicts the same scene as the left image, however, corrected using scaled ghosting correction as provided by the present invention, and showing a reduced or vanished artefact.

Figure 3:
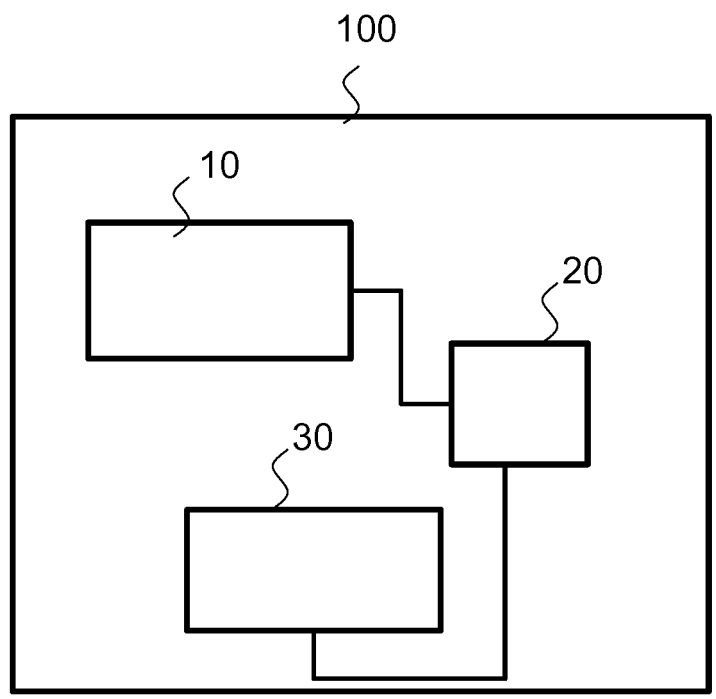
FIG. 3 shows a schematic diagram of a device for signal compensation according to an exemplary embodiment of the present invention.

FIG. 3 shows a schematic diagram of a device for signal compensation according to an exemplary embodiment of the present invention. A device 100 for signal compensation may comprise a generation module 10, a scaling module 20, and a subtraction module 30. The generation module 10 may be configured to generate an X-ray ghosting image based on detector read-out prior to an X-ray exposure and/or on detector readout after the X-ray exposure. The scaling module 20 may be configured to scale the X-ray ghosting image into a scaled ghosting image. The subtraction module 30 may be configured to subtract the scaled X-ray ghosting image from an X-ray image of the patient recorded during the X-ray exposure.

Figure 4:
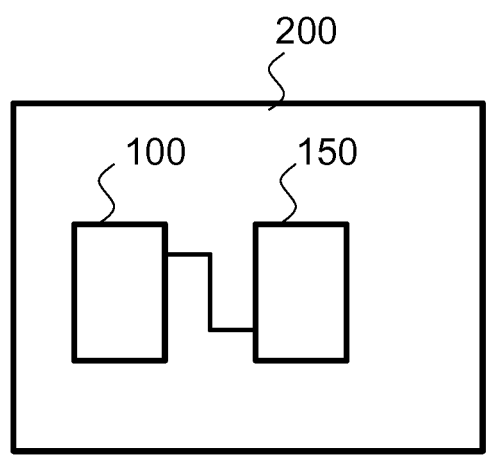
FIG. 4 shows a schematic diagram of a medical imaging system according to an exemplary embodiment of the present invention.

FIG. 4 shows a schematic diagram of a medical imaging system according to an exemplary embodiment of the present invention. A medical imaging system 200 may comprise a flat panel X-ray detector 150 and a device 100 for signal compensation. The medical imaging system 200 may be a digital radiography system. Digital radiography uses a digital X-ray detector also referred to as flat panel X-ray detector. The digital X-ray detector of the medical imaging system 200 may typically show significant lag signals in areas exposed to more than ~100 μGy, which level of exposure frequently occurs in stitching exposures.

The present invention advantageously provides that the hardware of mid- and low-end detectors is kept as simple as possible, meaning that hardware devices to reduce lag are omitted. Therefore, the present invention advantageously applies powerful image processing algorithms to reduce lag visibility. The scaling of the lag signal which is proposed here leads to significant improvements.

Figure 5:
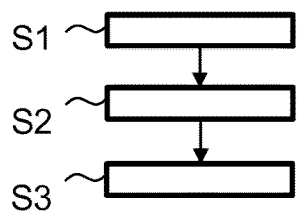
FIG. 5 shows a schematic flow-chart diagram of a method for signal compensation according to a further exemplary embodiment of the present invention

FIG. 5 shows a schematic flow-chart diagram of a method for signal compensation according to a further exemplary embodiment of the present invention. As a first step of the method, generating S1 an X-ray ghosting image based on detector read-out prior to an X-ray exposure and/or based on detector read-out subsequent to the X-ray exposure by means of a generation module 10 is performed. As a second step of the method, scaling S2 the X-ray ghosting image into a scaled X-ray ghosting image by means of a scaling module 20 may be conducted. As a third step of the method, subtracting S3 the scaled X-ray ghosting image from a recorded X-ray image of the patient by means of a subtraction module 30 may be performed.

The method for signal compensation allows correcting the ghosting artifact by minimizing the image variance in the boundary area of the artifact. Since the artifact is an additional structure in the image, the image variance is minimized if the artifact vanishes. This ensures optimal minimization of the contrast of the former direct radiation areas without calibration of the material properties of the detector.

Figure 6:
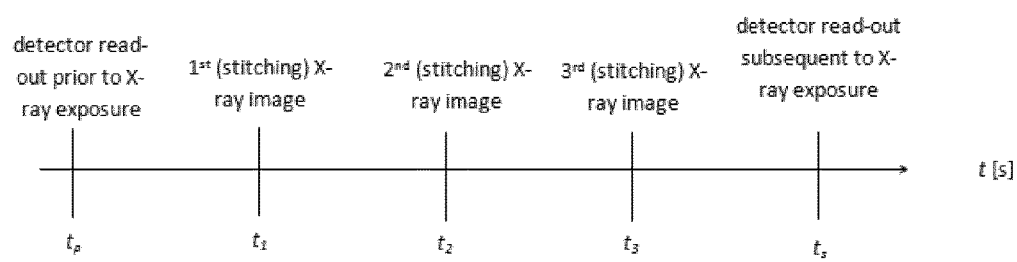
FIG. 6 shows a timing diagram with indication of time points at which images are recorded for explaining the present invention.

FIG. 6 shows a timing diagram depicting the following points in time with respect to three consecutive X-ray images. Herein $t_p$ refers to a point in time at which a detector read-out prior to X-ray exposure is recorded; $t_1$ refers to a point in time at which the first X-ray exposure (high dose image causing the lag artefact) is recorded to generate a first g X-ray image; $t_2$ refers to a point in time at which a second X-ray exposure is recorded to generate a second X-ray image (containing the lag artefact); $t_3$ refers to a point in time at which a third X-ray exposure is recorded to generate a third X-ray image (containing the lag artefact but typically to a lesser extent), and $t_s$ refers to a point in time at which a detector read-out subsequent to X-ray exposure is recorded containing a (stable) offset reference signal (due to the X-ray detector) and a decayed lag artefact. The X-ray exposures of this exemplary embodiment may be generated using an X-ray source known per se to the person skilled in the art. The first, second and third X-ray exposures may be first, second and third stitching X-ray exposures, respectively. Consequently, the first, second and third X-ray images may be first, second and third stitching X-ray images, respectively, which may subsequently be stitched into a joined X-ray image based on overlapping fields of view. In FIG. 6 it holds that $t_p < t_1 < t_2 < t_3 < t_s$.

According to an exemplary embodiment, with reference to FIG. 6, the scaling factor in respect of the second (stitching) X-ray image may be calculated as:

$$\text{scaling factor} = \left(\frac{t_s - t_1}{t_2 - t_1}\right)^\lambda \quad \text{Equation 1}$$

wherein $\lambda$ (with $\lambda > 0$) is a model specific parameter for the X-ray detector at hand determinable by measurement. Similarly, the scaling factor in respect of the third (stitching) X-ray image may be calculated as:

$$\text{scaling factor} = \left(\frac{t_s - t_1}{t_3 - t_1}\right)^\lambda \quad \text{Equation 2}$$

Figure 7:
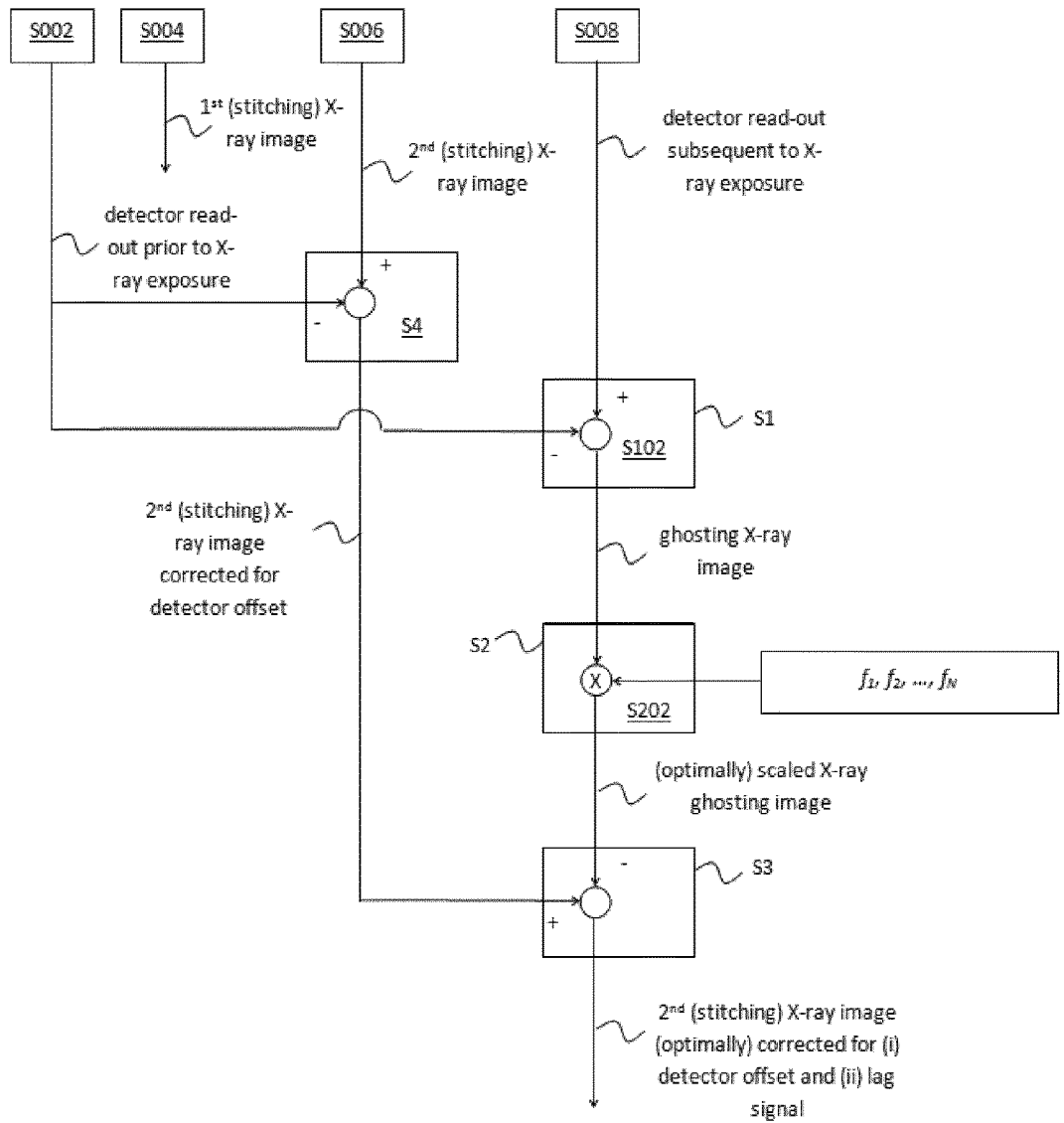
FIG. 7 shows a schematic flow-chart diagram of a process for image processing according to an exemplary embodiment of the present invention.

FIG. 7 shows a schematic flow-chart diagram of a method for image processing according to an exemplary embodiment of the present invention, which method allows for execution by a device according to an exemplary embodiment of the present invention.

The exemplary embodiment of FIG. 7 allows for very effective application in stitching applications. An exemplary embodiment of the present invention concerns stitching of two consecutive X-ray images from one and same patient having a partially overlapping field of view, which two X-ray images are acquired subsequently with a movable flat-panel X-ray detector ("FPD"). The two X-ray images are "stitched together" into a joined X-ray image by image processing to allow depiction of body parts that exceed the dimensions of the movable FPD. A notable example is in depicting the entire spine in the joined X-ray image.

According to an exemplary embodiment of the present invention, the first and second stitching X-ray exposures need to be carried out with a minimal time there between in order to minimize the effects of patient movement. The first stitching X-ray exposure may cause image lag in the second stitching X-ray image as generated by the second stitching X-ray exposure, which image lag is not well corrected by all known methods.

Alternatively, the exemplary embodiment depicted in FIG. 7 allows for equally effective use in applications other than stitching. Consequently, in the following description of the embodiment displayed in FIG. 7, each occurrence of "(stitching)" indicates the optional use for stitching applications.

The X-ray exposures of this exemplary embodiment may be generated using an X-ray source known per se to the person skilled in the art. With reference to FIG. 7, in this example in step S002, at $t = t_p$, an X-ray detector read-out prior X-ray exposure is recorded in order to acquire an offset image free of lag. This serves separating the lag signal recorded at a later instance from the undisturbed offset signal. The start-up phase of an X-ray imaging system typically will allow for performing step S002. In this example, in steps S004 and S006 first and second (stitching) X-ray images are acquired in response to first and second (stitching) X-ray exposures at $t = t_1$ and $t = t_2$, respectively. In this example, in step S008, at $t = t_s$, an X-ray detector read-out (containing the offset reference signal and a decayed lag artifact) subsequent to the second (stitching) X-ray exposure is recorded. Herein $t_p < t_1 < t_2 < t_s$.

In this example, in step S4, an offset corrected second (stitching) X-ray image is generated by subtracting, from the second (stitching) X-ray image, the detector read-out acquired during step S002.

Step S1, which may be performed by the generation module 10, comprises generating an X-ray ghosting image. In this example, step S1 for that purpose comprises a step S102 for subtracting, from the X-ray detector read-out acquired during step S002, the X-ray detector read-out acquired during step S008. In other words: in step S102 the lag artifact is being offset corrected.

In step S2, which may be performed by the scaling module 20, the scaled X-ray ghosting image is generated. In this example, step S2 for that purpose comprises a step S202 for multiplying the X-ray ghosting image as generated in step S1 with a scaling. Optionally, step S202 comprises determining an optimal scaling. For example step S202 comprises (i) calculating for a range of N scaling factors $f_1, \ldots f_N$, the variances that would respectively be obtained for the second (stitching) X-ray image after correction; and (ii) subsequently selecting a scaling factor $f_i$ such that aforementioned variance is minimized. An approximate value for the optimum scaling may be calculated from the acquisition times $t_1$, $t_2$ and $t_s$ since the typical temporal decay of the lag signal is measured during detector qualification. For example, the range of N scaling factors $f_1, \ldots f_N$ may be derived using Equation 1.

In step S3, which may be performed by the subtraction module 30, the ghosting in the second (stitching) X-ray image is reduced by subtracting, from the offset corrected second (stitching) X-ray image as obtained in step S4, the scaled X-ray ghosting image generated in step S2 (which image may be optimally scaled in step S202). The result of step S3 is a second (stitching) X-ray image, corrected for X-ray detector offset as well as lag signal, which image may subsequently be stitched with the first (stitching) X-ray image into a joined X-ray image.

Figure 8:
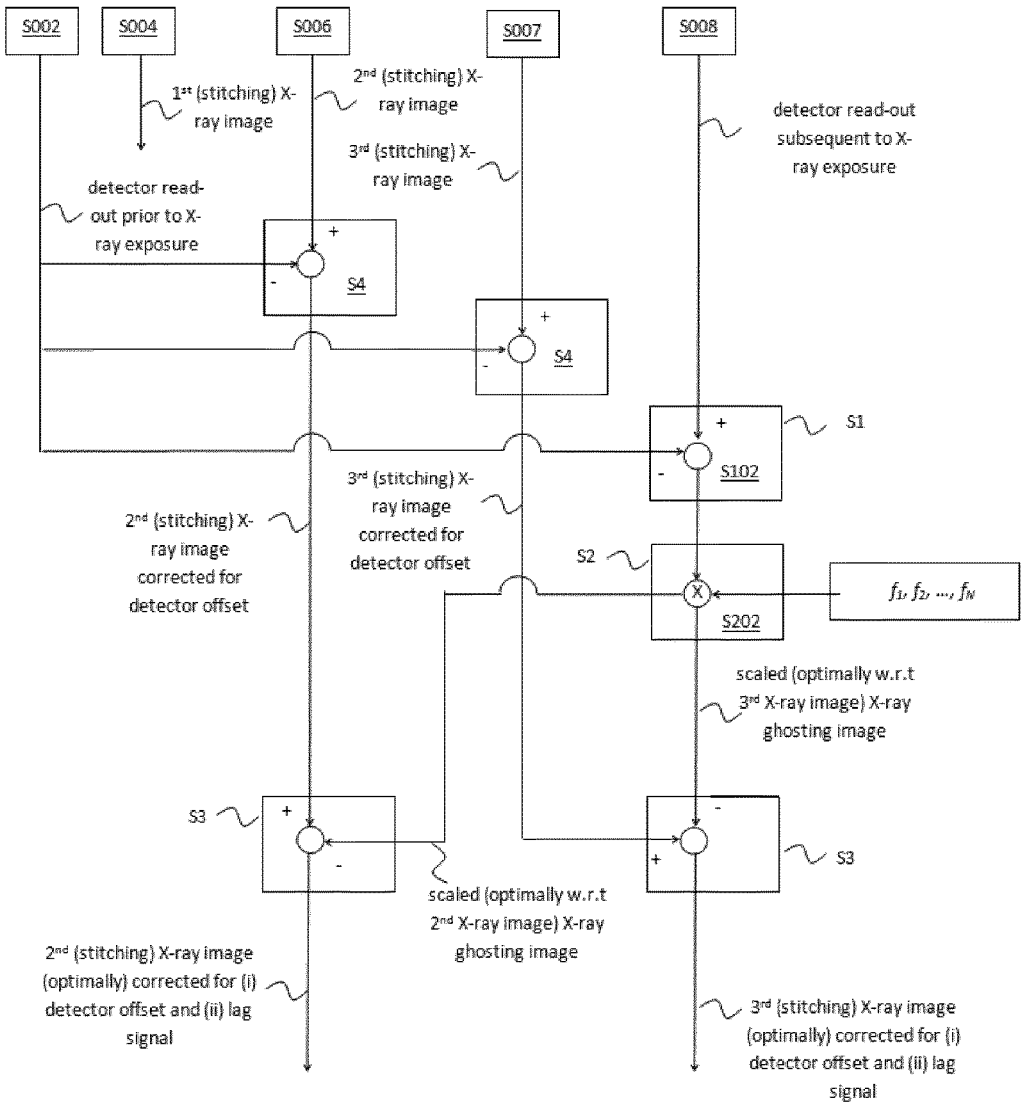
FIG. 8 shows a schematic flow-chart diagram of a process for image processing according to another exemplary embodiment of the present invention.

FIG. 8 shows a schematic flow-chart diagram of a method for image processing according to an exemplary embodiment of the present invention, which method allows for execution by a device according to an exemplary embodiment of the present invention.

The exemplary embodiment of FIG. 8 allows for very effective application in stitching applications. Alternatively, the exemplary embodiment depicted in FIG. 8 allows for equally effective use in applications other than stitching. Consequently, in the following description of the embodiment displayed in FIG. 8, each occurrence of "(stitching)"

indicates the optional use for stitching applications. The X-ray exposures of this exemplary embodiment may be generated using an X-ray source known per se to the person skilled in the art. In addition to the exemplary embodiment depicted in FIG. 4, this exemplary embodiment comprises a step S007 in which a third (stitching) X-ray images is acquired in response to a third (stitching) X-ray exposure at $t=t_s$. Herein $t_p<t_1<t_2<t_3<t_s$. Furthermore, in the embodiment depicted in FIG. 5, step S4 comprises acquiring an offset corrected third (stitching) X-ray image by subtracting, from the third (stitching) X-ray image, the detector read-out acquired during step S002.

In step S2, which may be performed by the scaling module 20, scaled X-ray ghosting images are generated. Step S2 for that purpose comprises a step S202 for multiplying the X-ray ghosting image as generated in step S1 with a scaling. Optionally, step S202 comprises determining an optimal scaling. For example step S202 comprises (i) calculating for a range of N scaling factors $f_1, \ldots f_N$, the variances that would be obtained in the second and third (stitching) X-ray images respectively after correction and (ii) subsequently selecting (a) a scaling factor $f_i$ such that the variance in the second (stitching) X-ray image is minimized and (b) a scaling factor $f_j$ such that the variance in the third (stitching) X-ray image is minimized. Herein, in general, it will hold that $f_i \neq f_j$. More specifically, since the lag signal decays with time, it will typically hold that $f_i > f_j$. An approximate value for the optimum scaling $f_i$ may be calculated from the acquisition times $t_1$, $t_2$ and $t_s$ since the typical temporal decay of the lag signal is measured during detector qualification. Likewise, An approximate value for the optimum scaling $f_j$ may be calculated from the acquisition times $t_1$, $t_3$ and $t_s$. For example, the range of N scaling factors $f_1, \ldots f_N$ may be derived using Equations 1 and 2.

In step S3, which may be performed by the subtraction module 30, the ghosting in the second and third (stitching) X-ray images is reduced. Ghosting in the second (stitching) X-ray image is reduced, by subtracting, from the offset corrected second (stitching) X-ray image as obtained in step S4, the scaled X-ray ghosting image generated in step S2 (which may be optimally scaled w.r.t. the second (stitching) X-ray image in step S202). Likewise ghosting in the third (stitching) X-ray image is reduced by subtracting, from the offset corrected third (stitching) X-ray image as obtained in step S4, the scaled X-ray ghosting image generated in step S2 (which may be optimally scaled w.r.t. the second (stitching) X-ray image in step S202).

The result of step S3 are second and third (stitching) X-ray images, both (optionally optimally) corrected for X-ray detector offset as well as lag signal. These images may subsequently be stitched with the first (stitching) X-ray image into a joined X-ray image. It should the exemplary embodiment depicted in FIG. 8 may be extended to cover (stitching) of more than three X-ray images.

Figure 9:
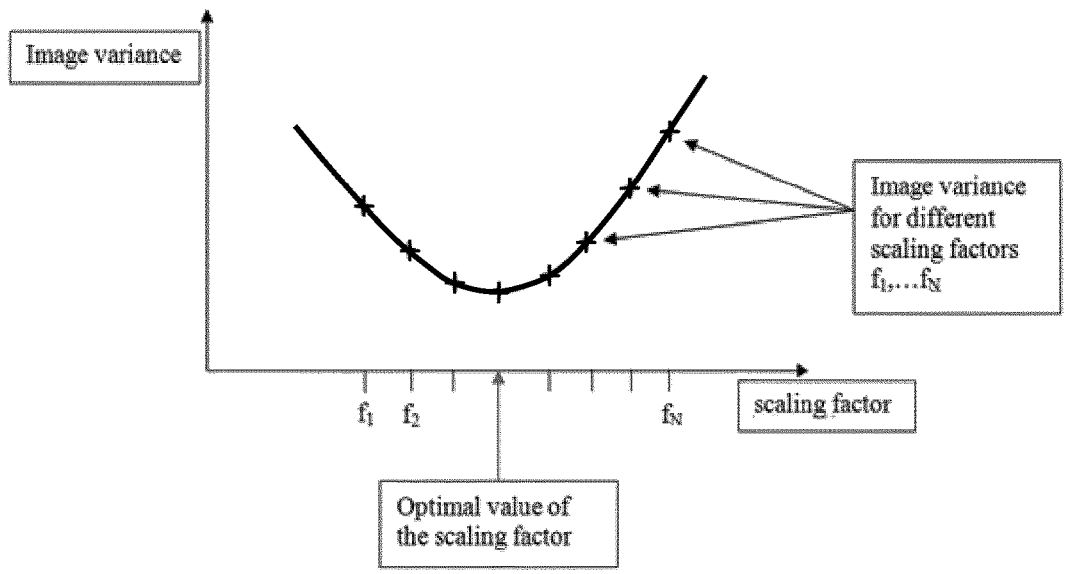
FIG. 9 shows a schematic diagram displaying the image variance versus the scaling factor according to an exemplary embodiment of the present invention.

FIG. 9 shows a schematic diagram displaying image variance as a function of scaling according to an exemplary embodiment of the present invention. For different values of the N scaling factors $f_1, \ldots f_N$,—as depicted on the horizontal axis—the variance in the image is calculated and displayed along the vertical axis. The optimal scaling factor minimizes the image variance.

Figure 10:
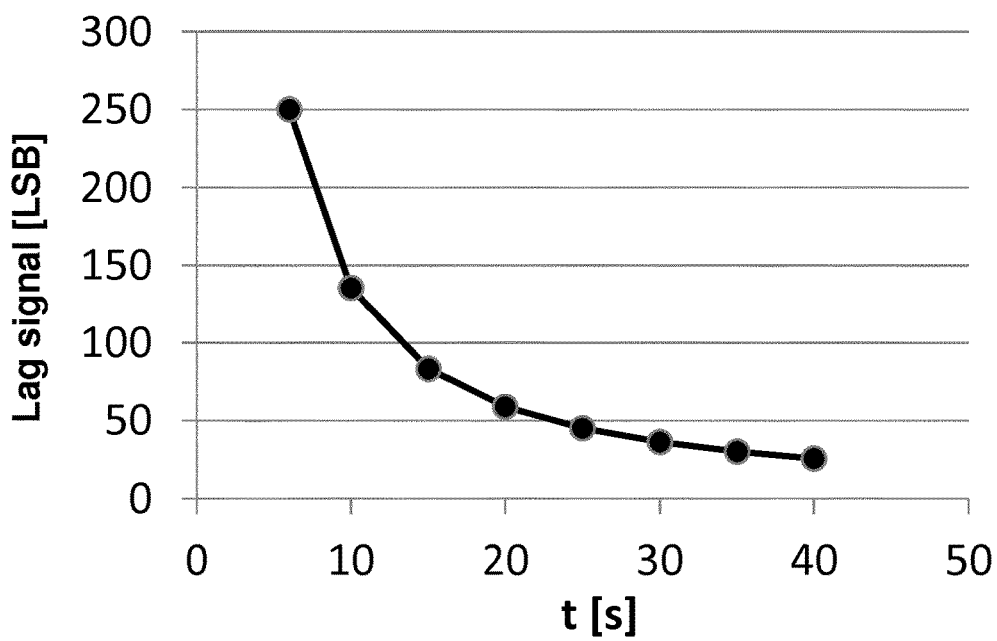
FIG. 10 shows a diagram with the temporal decay of a lag signal caused by a high dose exposure for explaining the present invention.

FIG. 10 schematically depicts the decay with time t for a lag signal, which lag signal is caused by a high dose X-ray exposure. Herein the y-axis shows the intensity of the signal S(t), i.e. the memory signal. Herein "LSB" is short for "least significant bit". The x-axis is used to represent the time t. In FIG. 10 a data point is connected to an image read-out, either a dark image or in response to an X-ray exposure. The data point earliest occurring in time is at $t=t_2$ i.e. the time of the second X-ray exposure.

With reference to the timing diagram depicted in FIG. 6, according to an exemplary embodiment of the present invention, the time-dependent decay of the lag (or ghosting) signal may be modeled by the expression $$S(t=t_s) = S(t=t_2) \cdot \left(\frac{t_2 - t_1}{t_s - t_1}\right)^\lambda \qquad \text{Equation 3}$$

wherein S(t) denotes the lag signal, at some time t, as present in the image read-out (either a dark image or in response to an X-ray exposure) at said some time $t > t_1$. The exponent λ is a model parameter, specific for a given X-ray detector, which may need to be determined by a previous measurement. Using this model it may be possible to back-extrapolate the lag signal present in the second X-ray image, using the lag signal present in the detector read-out subsequent to the last X-ray exposure:

$$S(t=t_2) = S(t=t_s) \cdot \left(\frac{t_s - t_1}{t_2 - t_1}\right)^\lambda \qquad \text{Equation 4}$$

Subtraction of this back-extrapolated lag signal from the second X-ray image may yield a much better correction of the lag signal. Such improved correction may be indispensable for radiographic imaging with a very short cycle time. By subtracting the detector read out prior to X-ray exposure from the detector read out subsequent to X-ray exposure, an image (more specifically a dark image) containing only the lag $S(t=t_s)$ may be determined. Subsequently Equation 4 may e.g. be used to back-extrapolate from S(t=t2) the lag image $S_2$ present in the X-ray image read-out in response to the second (stitching) X-ray exposure.

Likewise, using this model it may be possible to back-extrapolate the lag signal present in the third X-ray image:

$$S(t=t_3) = S(t=t_s) \cdot \left(\frac{t_s - t_1}{t_3 - t_1}\right)^\lambda \qquad \text{Equation 5}$$

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of subject-matter also any combination between features relating to different subject-matters is considered to be disclosed within this application. However, all features can be combined providing synergetic effects that are more than the simple summation of the features.

While the present invention has been illustrated and described in detail in the drawings and the foregoing description, such illustration and description are to be considered illustrative or exemplary and not restrictive; the present invention is not limited to the disclosed embodiments. As indicated, the present invention particular allows for successful application in stitching procedures, but certainly allows for successful application in procedures in which subsequent X-ray images are not mutually stitched. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for processing signals in order to remove artefacts between consecutive X-ray images, the artefacts appearing due to high radiation doses and a short time between X-ray exposures of the consecutive X-ray images, the device comprising:
    a processor configured to:
        generate an X-ray ghosting image based on an X-ray detector read-out subsequent to a last X-ray exposure of a plurality of X-ray exposures;
        scale the X-ray ghosting image to obtain a scaled X-ray ghosting image using a scaling operation that is different for each subsequent X-ray image, wherein the scaling operation is a function of the time-dependent decay of the X-ray ghosting image; and
        subtract each of the scaled X-ray ghosting images from each of the corresponding subsequent X-ray images obtained during a respective subsequent X-ray exposure of the plurality of X-ray exposures.

2. The device according to claim 1, wherein the X-ray ghosting image is generated based on an X-ray detector read-out prior to a first X-ray exposure of the plurality of X-ray exposures.

3. The device according to claim 2, wherein the X-ray detector read-out prior to the first X-ray exposure is subtracted from a first X-ray image recorded during the first X-ray exposure and/or from any subsequent X-ray image.

4. The device according to claim 1, wherein the scaling operation is (i) proportional to a time period between the X-ray detector read-out subsequent to the last X-ray exposure and the first X-ray exposure, and/or (ii) inversely proportional to a time period between the first X-ray exposure and any subsequent X-ray exposure.

5. The device according to claim 4, wherein the scaling operation is based on a time period between (i) the X-ray detector read-out subsequent to the last X-ray exposure and the first X-ray exposure, and/or (ii) the first X-ray exposure and the second X-ray exposure.

6. The device according to claim 5, wherein the scaling operation is based on minimization of a calculated image variance of at least one subsequent X-ray image.

7. A medical imaging system, comprising:
    a flat panel X-ray detector; and
    a device for processing signals in order to remove artefacts between consecutive X-ray images, the artefacts appearing due to high radiation doses and a short time between X-ray exposures of the consecutive X-ray images, the device comprising:
        a processor configured to:
            generate an X-ray ghosting image based on an X-ray detector read-out subsequent to a last X-ray exposure of a plurality of X-ray exposures;
            scale the X-ray ghosting image to obtain a scaled X-ray ghosting image using a scaling operation that is different for each subsequent X-ray image, wherein the scaling operation is a function of the time-dependent decay of the X-ray ghosting image; and
            subtract each of the scaled X-ray ghosting images from each of the corresponding subsequent X-ray images obtained during a respective subsequent X-ray exposure of the plurality of X-ray exposures.

8. The medical imaging system according to claim 7, further comprising image stitching by combining a plurality of X-ray images having partially overlapping fields of view to produce a joined X-ray image.

9. A method for processing signals in order to remove artefacts between consecutive X-ray images, the artefacts appearing due to high radiation doses and a short time between X-ray exposures of the consecutive X-ray images, the method comprising:
    generating, by a processor, an X-ray ghosting image based on an X-ray detector read-out subsequent to a last X-ray exposure of a plurality of X-ray exposures;
    scaling, the X-ray ghosting image to obtain a scaled X-ray ghosting image using a scaling operation that is different for each subsequent X-ray image, wherein the scaling operation is a function of the time-dependent decay of the X-ray ghosting image; and
    subtracting each of the scaled X-ray ghosting images from each of the corresponding subsequent X-ray images obtained during a respective subsequent X-ray exposure of the plurality of X-ray exposures.

10. The method according to claim 9, further comprising generating the X-ray ghosting image based on an X-ray detector read-out prior to a first X-ray exposure of the plurality of X-ray exposures.

11. The method according to claim 9, further comprising subtracting the X-ray detector read-out prior to the first X-ray exposure from a first X-ray image recorded during the first X-ray exposure and/or from any subsequent X-ray image.

12. The method according to claim 9, wherein the scaling operation is based on minimization of a calculated image variance of at least one subsequent X-ray image.

13. A non-transitory computer-readable medium having one or more executable instructions stored thereon, which when executed by a processor, cause the processor to perform a method for processing signals in order to remove artefacts between consecutive X-ray images, the artefacts appearing due to high radiation doses and a short time between X-ray exposures of the consecutive X-ray images, the method comprising:
    generating an X-ray ghosting image based on an X-ray detector read-out subsequent to a last X-ray exposure of a plurality of X-ray exposures;
    scaling the X-ray ghosting image to obtain a scaled X-ray ghosting image using a scaling operation that is different for each subsequent X-ray image, wherein the scaling operation is a function of the time-dependent decay of the X-ray ghosting image; and
    subtracting each of the scaled X-ray ghosting images from each of the corresponding subsequent X-ray images obtained during a respective subsequent X-ray exposure of the plurality of X-ray exposures.

* * * * *